(12) United States Patent
Autran et al.

(10) Patent No.: US 8,198,200 B2
(45) Date of Patent: *Jun. 12, 2012

(54) WEB MATERIALS HAVING BOTH PLASTIC AND ELASTIC PROPERTIES

(75) Inventors: Jean-Philippe Marie Autran, Wyoming, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 60 days.

This patent is subject to a terminal disclaimer.

(21) Appl. No.: 11/087,933

(22) Filed: Mar. 23, 2005

(65) Prior Publication Data

US 2005/0215964 A1    Sep. 29, 2005

Related U.S. Application Data

(60) Provisional application No. 60/557,225, filed on Mar. 29, 2004.

(51) Int. Cl.
*D04H 1/00* (2006.01)
(52) U.S. Cl. .................. 442/328; 442/329; 525/191
(58) Field of Classification Search .......... 442/328–329; 525/191

See application file for complete search history.

(56) References Cited

U.S. PATENT DOCUMENTS

| | | |
|---|---|---|
| 2,413,970 A | 1/1947 | Thomas |
| 3,848,594 A | 11/1974 | Buell |
| 3,860,003 A | 1/1975 | Buell |
| 4,322,467 A | 3/1982 | Heimbach et al. |
| 4,342,314 A | 8/1982 | Radel et al. |
| 4,515,595 A | 5/1985 | Kievit et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,699,622 A | 10/1987 | Toussant et al. |
| 4,705,584 A | 11/1987 | Lauchenauer |
| 4,834,735 A | 5/1989 | Alemany et al. |
| 4,846,815 A | 7/1989 | Scripps |
| 4,888,231 A | 12/1989 | Angstadt |
| 4,892,536 A | 1/1990 | DesMarais et al. |

(Continued)

FOREIGN PATENT DOCUMENTS

DE    19516037 A1    11/1996

(Continued)

OTHER PUBLICATIONS

Greg Hearn, Multistrand Elastics' Role in Diaper Performance, Nonwovens World, Apr.-May 2003, pp. 63-68.
Simulations on Crystallization in Stereoblock Poly(propylene). Idealized Structures Showing the Effects of Atactic Block Length, Macromol. Theory Simul. 7, 69-77 (1998), Huthig & Wepf Verlag, Zug.

*Primary Examiner* — Elizabeth Cole
(74) *Attorney, Agent, or Firm* — Charles R. Ware (57) ABSTRACT

An extruded web is disclosed. The extruded web can be either a nonwoven material of a films. The web comprises a plasto-elastic material where the plasto-elastic material is a combination of a first polyolefin and a second polyolefin (either a polymeric blends or a polymeric mixture). The claimed combination of polyolefins results in a material that has substantially plastic properties when a sample taken from said web is subjected to an initial strain cycle (such that the web is provided with a set of at least 30% by an initial strain cycle) and substantially elastic properties when a sample taken from the web is subjected to at least a second strain cycle.

14 Claims, 1 Drawing Sheet

U.S. PATENT DOCUMENTS

| | | | |
|---|---|---|---|
| 4,894,060 A | 1/1990 | Nestegard | |
| 4,940,464 A | 7/1990 | Van Gompel et al. | |
| 4,946,527 A | 8/1990 | Battrell | |
| 4,963,140 A | 10/1990 | Robertson et al. | |
| 4,990,147 A | 2/1991 | Freeland | |
| 5,037,416 A | 8/1991 | Allen et al. | |
| 5,055,103 A | 10/1991 | Nomura et al. | |
| 5,057,097 A | 10/1991 | Gesp | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell | |
| 5,156,793 A | 10/1992 | Buell et al. | |
| 5,167,897 A | 12/1992 | Weber et al. | |
| 5,217,798 A | 6/1993 | Brady et al. | |
| 5,221,274 A | 6/1993 | Buell | |
| 5,236,430 A | 8/1993 | Bridges | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,302,454 A | 4/1994 | Cecchin et al. | |
| 5,330,598 A | 7/1994 | Erdman et al. | |
| 5,342,338 A | 8/1994 | Roe | |
| 5,368,584 A | 11/1994 | Clear et al. | |
| 5,387,207 A | 2/1995 | Dyer et al. | |
| 5,397,316 A | 3/1995 | LaVon et al. | |
| H1517 H | 2/1996 | Erickson et al. | |
| 5,499,978 A | 3/1996 | Buell et al. | |
| 5,507,736 A | 4/1996 | Clear et al. | |
| 5,542,942 A | 8/1996 | Kline et al. | |
| 5,547,736 A | 8/1996 | Simon et al. | |
| 5,554,143 A | 9/1996 | Roe et al. | |
| 5,554,144 A | 9/1996 | Roe et al. | |
| 5,554,145 A | 9/1996 | Roe et al. | |
| 5,556,394 A | 9/1996 | Roe et al. | |
| 5,569,232 A | 10/1996 | Roe et al. | |
| 5,569,234 A | 10/1996 | Buell et al. | |
| 5,571,096 A | 11/1996 | Dobrin et al. | |
| 5,575,783 A | 11/1996 | Clear et al. | |
| 5,580,411 A | 12/1996 | Nease et al. | |
| 5,591,152 A | 1/1997 | Buell et al. | |
| 5,594,080 A * | 1/1997 | Waymouth et al. | 526/126 |
| 5,650,222 A | 7/1997 | DesMarais et al. | |
| 5,662,758 A | 9/1997 | Hamilton et al. | |
| 5,669,897 A | 9/1997 | Lavon et al. | |
| 5,671,678 A | 9/1997 | Bolte et al. | |
| 5,749,865 A | 5/1998 | Yamamoto et al. | |
| 5,749,866 A | 5/1998 | Roe et al. | |
| H1750 H | 9/1998 | Dobrin | |
| 5,865,823 A | 2/1999 | Curro | |
| 5,871,607 A | 2/1999 | Hamilton et al. | |
| 5,876,391 A | 3/1999 | Roe et al. | |
| 5,897,545 A | 4/1999 | Kline et al. | |
| 5,904,673 A | 5/1999 | Roe et al. | |
| 5,910,224 A | 6/1999 | Morman | |
| 5,916,663 A | 6/1999 | Chappell et al. | |
| 5,957,908 A | 9/1999 | Kline et al. | |
| 6,004,306 A | 12/1999 | Robles et al. | |
| 6,050,985 A | 4/2000 | Lavon et al. | |
| 6,107,537 A | 8/2000 | Elder et al. | |
| 6,120,487 A | 9/2000 | Ashton | |
| 6,120,489 A | 9/2000 | Johnson et al. | |
| 6,132,409 A | 10/2000 | Vogt et al. | |
| 6,168,584 B1 | 1/2001 | Allen et al. | |
| 6,193,701 B1 | 2/2001 | Van Gompel et al. | |
| 6,193,918 B1 | 2/2001 | McGuire et al. | |
| 6,245,050 B1 | 6/2001 | Odorzynski et al. | |
| 6,303,208 B1 | 10/2001 | Pelkie | |
| 6,313,372 B1 | 11/2001 | Suzuki | |
| 6,325,787 B1 | 12/2001 | Roe et al. | |
| 6,429,352 B1 | 8/2002 | Herrlein et al. | |
| 6,432,098 B1 | 8/2002 | Kline et al. | |
| 6,436,512 B1 | 8/2002 | Kauschke et al. | |
| 6,448,464 B1 | 9/2002 | Akin et al. | |
| 6,465,073 B1 | 10/2002 | Morman et al. | |
| 6,478,785 B1 | 11/2002 | Ashton et al. | |
| 6,495,229 B1 | 12/2002 | Carte et al. | |
| 6,503,236 B1 | 1/2003 | Uitenbroek et al. | |
| 6,531,025 B1 | 3/2003 | Lender et al. | |
| 6,531,027 B1 | 3/2003 | Lender et al. | |
| 6,552,245 B1 | 4/2003 | Roessler et al. | |
| 6,585,713 B1 | 7/2003 | LeMahieu et al. | |
| 6,623,468 B2 | 9/2003 | Shimoe | |
| 6,677,038 B1 | 1/2004 | Topolkaraev et al. | |
| 6,680,265 B1 | 1/2004 | Smith et al. | |
| 6,682,514 B1 | 1/2004 | Brunner | |
| 6,686,303 B1 | 2/2004 | Havnes et al. | |
| 6,703,537 B1 | 3/2004 | Roe et al. | |
| 6,827,806 B2 | 12/2004 | Uitenbroek et al. | |
| 6,833,179 B2 | 12/2004 | May et al. | |
| 6,875,710 B2 | 4/2005 | Eaton et al. | |
| 6,896,843 B2 | 5/2005 | Topolkaraev et al. | |
| 6,939,334 B2 | 9/2005 | Odorzynski et al. | |
| 6,994,761 B2 | 2/2006 | Klemp et al. | |
| 2002/0007164 A1 | 1/2002 | Boggs et al. | |
| 2002/0009940 A1 | 1/2002 | May et al. | |
| 2002/0128617 A1 | 9/2002 | Roe et al. | |
| 2002/0180097 A1 | 12/2002 | Giachetto et al. | |
| 2003/0083635 A1 | 5/2003 | Gibbs | |
| 2003/0084996 A1 | 5/2003 | Alberg et al. | |
| 2003/0087059 A1 | 5/2003 | Jackson et al. | |
| 2003/0087098 A1 | 5/2003 | Eaton et al. | |
| 2003/0088220 A1 | 5/2003 | Molander et al. | |
| 2003/0088228 A1 | 5/2003 | Desai et al. | |
| 2003/0091807 A1 | 5/2003 | Desai et al. | |
| 2003/0153894 A1 | 8/2003 | Gibbs et al. | |
| 2003/0204017 A1 | 10/2003 | Stevens et al. | |
| 2003/0233082 A1 | 12/2003 | Kline et al. | |
| 2004/0019139 A1 | 1/2004 | Hanke et al. | |
| 2004/0024109 A1 | 2/2004 | Hamersky et al. | |
| 2004/0044323 A1 | 3/2004 | Roessler et al. | |
| 2004/0049836 A1 | 3/2004 | Ashraf et al. | |
| 2004/0078018 A1 | 4/2004 | Gompel et al. | |
| 2004/0087235 A1 | 5/2004 | Morman et al. | |
| 2004/0106723 A1 | 6/2004 | Yang et al. | |
| 2004/0110442 A1 | 6/2004 | Rhim et al. | |
| 2004/0122408 A1 | 6/2004 | Potnis et al. | |
| 2004/0122409 A1 | 6/2004 | Thomas et al. | |
| 2004/0126579 A1 | 7/2004 | Creagan | |
| 2004/0127128 A1 | 7/2004 | Thomas | |
| 2004/0127131 A1 | 7/2004 | Potnis | |
| 2004/0127881 A1 | 7/2004 | Stevens et al. | |
| 2004/0134596 A1 | 7/2004 | Rosati et al. | |
| 2004/0142110 A1 | 7/2004 | Branca et al. | |
| 2005/0211368 A1 | 9/2005 | McGuire et al. | |
| 2005/0215963 A1 | 9/2005 | Autran et al. | |
| 2005/0215970 A1 | 9/2005 | Kline et al. | |
| 2005/0215971 A1 | 9/2005 | Roe et al. | |
| 2005/0215972 A1 | 9/2005 | Roe et al. | |
| 2005/0215973 A1 | 9/2005 | Roe et al. | |
| 2008/0091160 A1 | 4/2008 | Roe et al. | |
| 2008/0103473 A1 | 5/2008 | Roe et al. | |
| 2008/0147036 A1 | 6/2008 | Roe et al. | |
| 2008/0192480 A1 | 8/2008 | Rizkin et al. | |
| 2008/0262457 A1 | 10/2008 | Roe et al. | |

FOREIGN PATENT DOCUMENTS

| | | |
|---|---|---|
| EP | 0 472 942 B1 | 9/1995 |
| EP | 0 745 433 B1 | 12/1996 |
| EP | 1 081 672 A2 | 3/2001 |
| JP | 07 08912 | 4/1995 |
| JP | 07089012 | 4/1995 |
| JP | 10 53963 | 2/1998 |
| JP | 10-053963 | 2/1998 |
| WO | WO 94/01507 A1 | 1/1994 |
| WO | WO 95/16746 A1 | 6/1995 |
| WO | WO 96/24485 A1 | 8/1996 |
| WO | WO 97/47264 A1 | 12/1997 |
| WO | WO 98/46180 A1 | 10/1998 |
| WO | WO 01/27373 A1 | 4/2001 |
| WO | WO 02/060368 A2 | 8/2002 |
| WO | WO 03/039421 A | 5/2003 |

* cited by examiner

WEB MATERIALS HAVING BOTH PLASTIC AND ELASTIC PROPERTIES

CROSS REFERENCE TO RELATED APPLICATIONS

This application claims the benefit of U.S. Provisional Application No. 60/557,225 filed Mar. 29, 2004.

FIELD OF THE INVENTION

The present invention generally relates to web materials suitable for use in construction of disposable absorbent articles such as diapers, pull-on diapers, training pants, sanitary napkins, wipes, bibs, incontinence briefs or inserts and the like. More specifically, the invention is directed to web materials that have both plastic and elastic properties. Such materials may be used in the absorbent articles of the invention to provide the desired article shape and/or to impart the desired stress and strain properties for improved fit and comfort of the article on the wearer and/or for increased convenience of the user.

BACKGROUND OF THE INVENTION

Disposable absorbent products, such as diapers, training pants, and incontinence articles typically include stretchable materials, such as elastic strands, in the waist region and the cuff regions to provide a snug fit and a good seal of the article. Pant-type absorbent articles further include stretchable materials in the side portions for easy application and removal of the article and for sustained fit of the article. Stretchable materials have also been used in the ear portions of disposable diapers for adjustable fit of the article. However, it would be desirable to have materials that exhibit substantially plastic behavior prior to and during a shaping strain cycle, for example, when the article is initially put on a wearer, yet exhibit substantially elastic behavior after this initial shaping or donning strain cycle on the article. In this way, such desirable absorbent articles would have the ability to shape or size to the wearer to better fit conform to a wearer's body shape, yet have the ability to maintain the required tension when on a wearer to achieve sustained fit and prevent sagging and/or drooping of the article. Absorbent articles of this kind would allow the user or wearer to "permanently" adjust various areas of the absorbent article, e.g., the crotch or waist region of a diaper, either before or during the application of the article to the wearer, to adapt the article to a wearer's body shape. In the case of a diaper, better fit and comfort can also impart better functional performance such as reduced leakage since the diaper would be better fitting. Such features have heretofore not been available for absorbent articles.

There are various approaches to providing desirable stretchable properties in targeted areas of absorbent articles. Stretchable materials may be films or nonwoven fibrous webs that include elastomeric materials. Typically, such materials are stretchable in at least one, and possibly multiple, directions. However, because the films or webs are made entirely of elastomeric materials, they are relatively expensive, and they tend to have more drag on the skin surface, resulting in discomfort to a wearer of the article. Also, because the materials are elastomeric, any applied strain is substantially recovered when the force leading to the strain is removed. Sometimes, the stretchable films are laminated to one or more layers of nonwoven webs. Since typical nonwoven webs typically are made of thermoplastic fibers, they have very limited stretchability and, the resulting laminates provide considerable resistance to stretch without additional processing. It is necessary to reduce this resistance substantially in order to make functional stretch laminates. As a result, such materials have limited ability to shape, size or conform to the particularities of the wearer's anatomy upon application.

Other approaches to make stretchable materials are also known, including: stretch-bonded laminates (SBL) and necked-bonded laminates (NBL). Stretch bonded laminates are made by stretching an elastomeric material in the machine direction (MD), laminating it to one or more nonwoven substrates while it is in the stretched state, and releasing the tension in the elastomeric material so that the nonwovens gather and take on a puckered shape. Necked-bonded laminates are made by first stretching a nonwoven substrate in the machine direction such that it necks (i.e., reduces its dimension) at least in the cross machine direction (CD), then bonding the elastomeric material to the substrate while the substrate is still in the stretched, necked state. This laminate will be stretchable in the CD, at least up to the original width of the nonwoven before it was necked. Combinations of stretch bonding and neck bonding have also been known to deliver stretch in both MD and CD directions. In these approaches, at least one of the components is in a tensioned (i.e., stretched) state when the components of the laminates are joined together. Again, these materials cannot be used in absorbent articles to impart sizing or shaping features desired by users and wearers of absorbent articles.

Zero strain stretch laminates are also known. The zero strain stretch laminates are made by bonding an elastomer to a nonwoven while both are in an unstrained state. The laminates are then incrementally stretched to impart stretch properties. The incrementally stretched laminates are stretchable only to the extent afforded by the non-recovered (i.e., residual) extensibility of the laminate. For example, U.S. Pat. No. 5,156,793, issued to Buell et al., discloses a method for incrementally stretching an elastomer-nonwoven laminate web, in a non-uniform manner, to impart elasticity to the resulting laminate. These stretch laminates behave similarly to the materials described previously in that they do not have the inherent ability to be adapted to the size or shape of a wearer.

The art has also provided "elastic" materials by prestraining a substantially plastic film so as to provide films having an elastic-like behavior along at least one axis when subjected to an applied and subsequently released elongation. Such materials, known as Structural Elastic-Like Films (SELF), are described in U.S. Pat. No. 5,691,035 to Chappell.

However, in all the approaches above, the materials or laminates are made separately and then incorporated into the absorbent article. For example, the stretch laminates described herein must be cut into the appropriate size and shape, then adhesively attached to the desired location in the product in a process sometimes referred as the "cut-and-slip" process. Because of the different stretch properties required for different elements of the product, it is necessary to make a variety of laminates having different stretchability and cut the laminates to different sizes and shapes. Several cut and slip units may be needed to handle the different stretchability of the stretch laminates and to attach them to different locations of the product. As the number of cut-and-slip units and/or steps multiplies, the process quickly becomes cumbersome, complicated and expensive. These processes are suitable for modern day absorbent article manufacture and are desirable. However, it would therefore be desirable to have absorbent articles having the desired sizing and/or shaping properties, but which can be disposed in or on the absorbent article without the need for such complicated and expensive "cut-and-slip" processes.

One alternative to cut and slip processes used by the art is to print an elastomeric composition onto a substrate. Exemplary disclosures include U.S. Pat. No. 6,531,027 which discusses adhering components of an absorbent article using an adhesive printing process, PCT Application No. 03/039420 which discusses printing first and second elastomeric compositions onto a substrate where the compositions differ in at least one of the following properties: elasticity, melt viscosity, composition, shape, pattern, add-on level, and PCT Application No. WO 03/053308, which discusses printing an elastic adhesive onto an extendable substrate to provide a tensioning force during garment wear.

The polymer arts have provided materials with stretch properties that are useful in absorbent article structures. Such materials include:

Isotactic polypropylene with stereoerrors along the polymer chain as disclosed in U.S. Pat. No. 6,555,643 and EP 1 256 594 A1;

Blends of isotactic polypropylene and alpha-olefin/propylene copolymers as disclosed in U.S. Pat. Nos. 6,342,565 and 6,500,563 and WO 03/400201; and Block-like isotactic-atactic copolymers as disclosed in U.S. Pat. Nos. 6,559,262, 6,518,378 and 6,169,151.

Based on the foregoing, it would be desirable to have absorbent articles with stretchable material having both elastic and plastic properties such that it can be sized or shaped as desired but still retains the desired degree of elasticity to facilitate sustained fit on the wearer. Although not always necessary, it would be desirable to have such a material that can be disposed easily on any specific area of the absorbent article in any desired amount. Additionally, it would be desirable to have such a material or composite having plastic and elastic properties that can be easily placed in discrete, spaced apart areas of the absorbent article via known techniques such as a "cut-and-slip" process.

SUMMARY OF THE INVENTION

In one aspect of the invention, the plasto-elastic material has substantially plastic properties when it is subjected to an initial strain and having substantially elastic properties when it is subjected to a second strain cycle. In other aspects of the invention, the material used in the absorbent article has, according to a Hysteresis Test, at least about a 15% set upon a first application of a strain of 200%, and less than about a 15% set upon a second application of a strain of 50%. Typically, such materials also have a force at 25% elongation of between 0.005 N/cm and about 50 N/cm after the first application of a 200% strain.

In another aspect of the invention the plasto-elastic material is advantageously extruded into a fiber for use in a nonwoven material. Such fibers may comprise only the plasto-elastic material or they may be bicomponent fibers comprising at least one additional material. The additional material may be either a polymeric compound having substantially plastic stress-strain properties or the additional material may be a polymeric compound having substantially elastic properties.

In yet another aspect of the invention the plasto elastic material may be formed into a film structure using known extrusion techniques such as film casting and film blowing. Such films may comprise only the plasto-elastic material or they may be coextruded films comprising at least one additional material. The additional material may be either a polymeric compound having substantially plastic stress-strain properties or the additional material may be a polymeric compound having substantially elastic properties.

DETAILED DESCRIPTION OF THE INVENTION

Definitions

As used herein, the term "polymeric blend" means a mixture of polymers which includes, but is not limited to, homopolymers, copolymers (e.g., block, graft, random and alternating copolymers), terpolymers, etc., and blends and modifications thereof which is in the form of a solid solution, that is a homogeneous mixture. Optional adjuncts may be added to the polymeric blend and, if the blend remains a solid solution, such blends are also considered polymeric blends.

As used herein, the term "polymeric mixture" means a mixture of at least two polymeric materials, in which at least a portion of one or more of the polymeric materials is immiscible in at least a portion of another of the polymeric materials, i.e., the mixture is heterogeneous.

By "stretch", it is meant that the material has the ability to extend beyond its original length in at least one dimension when subjected to a tensile force (i.e., tension) applied in the direction of that dimension. "Stretch" may be unidirectional, bi-directional, or multi-directional. The specific "stretch" properties of a material may vary along any of the stretch vectors. As used herein, stretch includes both elastic and plastic deformation.

By "elastic" or "elasticity", it is meant that a material has the ability to return to substantially its original pre-stretched dimension after an elongation-relaxation cycle such as subjecting it to tension or a force in that dimension and then releasing the elongating tension on the material (i.e., allowing the material to relax).

By "plastic", "plasticity", "extensible", or "extensibility", it is meant that a material has the ability to elongate in at least one direction under an applied tensile force without significant return when the force is removed. Substantially non-recoverable deformation is referred to as plastic deformation.

By "plasto-elastic" and "plasto-elasticity", it is meant that a material has the ability to stretch in a substantially plastic manner during an initial strain cycle (i.e., applying a tensile force to induce strain in the material, then removing the force allowing the material to relax), yet exhibit substantially elastic behavior and recovery during subsequent strain cycles. It will also be recognized that an elasto-plastic material and elasto-plasticity are equivalent descriptors of such materials.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

"Longitudinal" is a direction running parallel to the maximum linear dimension of the article and includes directions within ±45° of the longitudinal direction. The "lateral" or "transverse" direction is orthogonal to the longitudinal direction. The "Z-direction" is orthogonal to both the longitudinal and transverse directions. The "x-y plane refers to the plane congruent with the longitudinal and transverse directions.

The term "substrate" as used herein refers to any material, including a film, an apertured film, a nonwoven web, a woven web, a foam or a combination thereof, or a dry lap material including wood pulp, cellulosic, derivatized or modified cellulosic materials, and the like, having a single layer or multiple layers. The term "fibrous substrate" as used herein refers to a material comprised of a multiplicity of fibers that could be either a natural or synthetic material or any combination thereof, including, for example, nonwoven materials, woven materials, knitted materials, and any combinations thereof.

The term "nonwoven" as used herein refers to a fabric made from continuous filaments and/or discontinuous fibers. Nonwoven fabrics include those made by carding staple fibers, airlaying or wet laying staple fibers and via extrusion processes such as spunbonding and melt blowing. The nonwoven fabric can comprise one or more nonwoven layers, wherein each layer can include continuous filaments or discontinuous fibers. Nonwovens can also comprise bi-component fibers, which can have shell/core, side-by-side, or other known fiber structures.

By "shaping strain cycle" is meant the steps of applying a tensile force to extend a plasto-elastic material to a desired elongation, then subsequently removing the tensile force and allowing the sample to relax, generating a substantial amount of permanent "set" or deformation in the material.

Preferred Embodiments

In a preferred embodiment, the invention provides a web of material which may be stretched into a new geometry, such as a larger size and/or different shape, substantially permanently, and thereafter, is elastic in that the larger sized or reshaped article may expand and substantially contract back to this new geometry. Such webs are particularly useful as materials for use in absorbent articles, such as diapers, pull-on diapers, training pants, sanitary napkins, wipes, bibs, incontinence briefs or inserts in that the article can be packaged, shipped and stored in a compact size for convenience prior to use, and then when used, removed from the package and expanded to be donned conveniently on the wearer. Once on the wearer, the article may be elastically expanded and contracted for good fit and comfort. In the context of this invention, the expansion or extendibility of the article when subjected to the initial stretch or pull can be referred to as the "plastic" deformation of the article in that the article substantially retains its new geometry. It should be understood that this new geometry does not need to be retained perfectly since those skilled in the art will appreciate that a certain amount of contraction and extensibility generally exists in most plastic materials. In other words, the permanency of the initial plastic deformation of the article sometimes may not perfect. In a similar fashion, the elasticity of the article upon subsequent stretch, pull or tension after the initial force also is not perfect, but like the initial plastic deformation, generally may be elastic at the plastically deformed new geometry of the article.

Stated differently, the present invention provides materials useful in absorbent articles that exhibit substantially plastic behavior prior to and during a shaping strain cycle, yet exhibit substantially elastic behavior after the initial shaping strain cycle during subsequent strain cycles. For example, an absorbent article may employ such a plasto-elastic material in its plastically deformable state (i.e., prior to a shaping strain cycle) such that the wearer or caregiver may selectively elongate at least a portion of the plasto-elastic material in a straining cycle to adapt the shape of the article for convenient donning and better fit for the wearer and to establish zones of post-straining cycle elasticity. Alternatively, at least a portion of the article's plasto-elastic material may be subjected to a shaping strain cycle to create a desired article shape and establish zones of elasticity after the shaping strain during manufacture of the article.

Plasto-Elastic Materials

A plasto-elastic material suitable for use in the absorbent article has, according to a Hysteresis Test described in more detail hereinafter, at least about a 15% set upon a first application of a strain of 200%, and less than about a 15% set upon a second application of a strain of 50%. Typically, plasto-elastic materials have at least about 30% set upon relaxation from an initial 200% strain. More preferably, plasto-elastic materials exhibit more than about 40% set, more preferably more than about 50%, and most preferably, more than about 70%. Such materials typically have a set between about 30% and about 140% after a first strain cycle of 200%, more typically between about 30% and about 120% and still more typically between about 40% and about 100%.

In subsequent strain cycles, the plasto-elastic materials of the present invention that have been prestrained to 200% exhibit less than about 15% set, preferably less than about 12% set and more preferably less than about 10% set after relaxation from a second strain of 50%.

Plasto-elastic materials also may exhibit low force relaxation when held in an at least partially extended state for an extended period of time in a strained configuration after a first strain cycle. Typical plasto-elastic materials that have been prestrained to 200% exhibit less than about 70% force relaxation, preferably less than about 60%, more preferably less than 50%, and most preferably less than about 40% while held at 50% strain for 4 hours at 38° C. The force relaxation behavior is similar when held in a strained configuration at lower temperatures. Specifically, prestrained (200%) plasto-elastic materials exhibit less than about 70% force relaxation, preferably less than about 60%, more preferably less than 50%, and most preferably less than about 40% while held at 50% strain for 30 seconds at 25° C.

Such desirable force relaxation behavior is particularly evident when the elastic component of the plasto-elastic material comprises more than one elastic material. As can be seen in Example 2, such blends can have the beneficial aspects of each of the constituent elastic materials.

Suitable materials have a force at 25% elongation of between 0.005 N/cm and about 50 N/cm after the first application of a 200% strain. Preferably the materials have a force at 25% strain of between about 0.05 N/cm and about 15 N/cm more preferably between about 0.01 N/cm and about 5 N/cm. In certain embodiments the elastic resistance ranges from about 0.1N to about 3 N/cm.

In order to help insure absorbent article features that are prestrained during the manufacturing process maintain their prestrained configuration throughout the distribution system, the plasto-elastic materials of the present invention preferably maintain their prestrained dimensions when exposed to elevated temperatures for extended times. Suitably, dimensions after a first strain cycle are reduced less than about 20% after unconstrained exposure to 60° C. for two minutes. Preferably, such dimensional reduction is less than about 15%, more preferably less than about 10%. Suitable plasto-elastic stretch materials comprise multi-component polyolefin compositions that comprise a combination of at least one elastic component and at least one component which causes the composition to exhibit plastic behavior during a first strain cycle. Such compositions are described more fully in the following sections.

Elastic Component

The elastic component functions to provide the desired amount and force of recovery upon the relaxation of an elongating tension on the plasto-elastic material, especially upon strain cycles following the initial shaping strain cycle. Many elastic materials are known in the art, including synthetic or natural rubbers (e.g., crosslinked polyisoprene, polybutadiene and their saturated versions (after hydrogenation) and polyisobutylene), thermoplastic elastomers based on either multi-block copolymers such as those comprising copolymerized rubber elastomeric blocks with polystyrene blocks (e.g., styrene/isoprene/styrene or styrene/butadiene/styrene) or polyurethanes, which form a hard glassy phase which when dispersed in the elastomeric phase, anchor the polymer chains together so as to provide high mechanical integrity. Preferred elastic components include ethylene and propylene-based elastomers.

Ethylene-rich elastomers may be polymerized with various amounts of comonomers more or less randomly incorporated in the backbone in order to significantly reduce the crystallinity of the ethylene-rich backbone. Unsaturation may also be incorporated along the chain to provide reactive sites for subsequent cross-linking or vulcanization reactions via sulfur chemistry or via exposure to radiation. Crosslinking reactions link polymeric chains to one another, resulting in greater shape recoverability by minimizing chain slippage that may lead to undesirable creep or stress relaxation. Ethylene-rich elastomers functionalized with small amounts of other chemical moieties may also provide sites for subsequent strong polar interactions (as in ionomers) or for subsequent crosslinking reactions (moisture-crosslinkable silane-modified polyethylene). Ethylene-rich elastomers having a tailored composition, molecular weight and narrow composition and molecular weight distributions may also be produced using metallocene-based catalysis. In other words, the amount of residual ethylene-based crystallinity may be controlled and can function as physical crosslinks and chain-anchoring entities capable of providing increased mechanical stability and integrity to the material.

Particularly preferred elastic components include propylene-rich elastomers. In these materials, propylene represents the majority component of the polymeric backbone, and as a result, any residual crystallinity possesses the characteristics of polypropylene crystals. As in the case of ethylene-based elastomers, residual crystalline entities embedded in the propylene-based elastomeric molecular network may function as physical crosslinks, providing polymeric chain anchoring capabilities that improve the mechanical properties of the elastic network, such as high recovery, low set and low force relaxation.

An alternative means of providing anchoring capabilities is to blend inorganic particles into an amorphous polymer matrix. Suitable particles may be either microscopic (equivalent diameter>0.1 microns) or nanoscopic (equivalent diameter<0.1 microns) in size. For example, the use of miocroscopic inorganic filler materials in polyolefin plastic components of the present invention may promote the formation of micropores during tensile loading and increase the moisture vapor transmission of the material which is beneficial to the internal climate of the disposable absorbent product.

Preferred elastomeric materials comprise polypropylene polymers and include:

a) Polypropylene polymers comprising crystalline isotactic blocks and amorphous atactic blocks. In this case the crystalline blocks serve as the "anchoring" points for the amorphous blocks that lie between such anchors. Such materials are disclosed, for example in U.S. Pat. Nos. 6,559,262, 6,518,378 and 6,169,151.

b) Isotactic polypropylene with stereoerrors along the polymer chain as disclosed in U.S. Pat. No. 6,555,643 and EP 1 256 594 A1.

c) Polypropylene polymers that incorporate a low level of a co monomer, such as ethylene or a higher α-olefin into the backbone to form an elastomeric random copolymer (RCP). Exemplary materials include: VISTAMAXX as is available from ExxonMobil Chemical Co. of Houston, Tex. and OLYMPUS as is available from the Dow Chemical Company of Midland, Mich.

In another embodiment of the present invention, the elastic component may comprise a blend of elastic materials. As noted above and in Example 2 such blends contribute particularly desirable force relaxation properties. In a particularly preferred embodiment of this type the elastic component comprise a combination of a polypropylene elastomer and a styrenic block copolymer.

Plastic Component

The plastic component of the plasto-elastic compositions of the present invention functions to provide the desired amount of permanent plastic deformation imparted to the material during the initial shaping strain cycle. The higher the concentration of a given plastic component in the plasto-elastic composition, the greater the possible permanent "set" following relaxation of an initial straining force on the material. Preferred plastic components include higher crystallinity polyolefins that are themselves intrinsically plastically deformable when subjected to a tensile force in one or more directions. Exemplary polyolefins of this type include certain linear low density polyethylenes (linear low density polyethylenes), high density polyethylenes (HDPEs), polypropylene homopolymers with and random copolymers of propylene and a small fraction of another monomer such as ethylene (plastic RCPs) having a melt temperature greater than about 80° C., multi-phase systems where a rubber is dispersed in a plastic phase also known as impact copolymers (ICPs), syndiotactic polypropylene, polybutene, polyolefin waxes and their blends. Suitable polyolefin plastic components may be either miscible or immiscible with the elastic component. Preferred polyolefin plastic component materials are at least partially immiscible with the material that constitutes the elastic component so as to facilitate the interpenetrating network discussed below. For example, in embodiments wherein the elastic component of the plasto-elastic material is of the stereoisomer type described above, a RCP matrix of intermediate crystallinity (low to medium ethylene content) is a preferred plastic component (e.g., WINTEC WFX4T available from Japan Polypropylene (Tokyo, Japan)). Alternatively, if the elastic component is of the random copolymer type, then a medium or high melt temperature polypropylene homopolymer or linear low density polyethylene is a preferred plastic component (e.g., ACHIEVE from ExxonMobil Chemical Company of Houston, Tex.).

Alternate polymorphic forms of the polyolefin plastic component may also be suitable. For example, beta-crystalline forms of polypropylene may provide an easily deformable, highly ductile, tough plastic component. Upon tensile deformation, beta-crystalline polypropylene may also develop microvoids, increasing the transport properties (e.g., the ability to transport water vapor therethrough) of the plastic component, and ultimately the plasto-elastic material.

A particularly preferred plastic component is a polyolefin wax. Suitable materials of this type include microcrystalline waxes, low molecular weight polyethylene waxes and polypropylene waxes. Such waxes are advantageously used between about 5% and about 50% of the plasto-elastic composition, preferably between about 10% and about 40%. Exemplary materials include but are not limited to: a microcrystalline wax available from the Crompton Corporation of Middlebury, Conn. as Multiwax W-835; a low melting refined petroleum wax available from the Chevron Texaco Global Lubricants of San Ramon, Calif. as Refined Wax 128; a low molecular weight polyethylene as is available from Honeywell Specialty wax and Additives of Morristown, N.J. as A-C 735 and a low molecular weight polypropylene as is available from Clariant, Pigments & Additives Division of Coventry, R.I. as Licowax PP230.

Plasto-Elastic Compositions

The structural and morphological characteristics of the elastic and plastic components within the plasto-elastic material, driven largely by the plasto-elastic blending process, are critical to the resultant stress-strain properties of the plasto-elastic material. Specifically, it is important to achieve microscale dispersion of any immiscible components (i.e., any discernable domains have an equivalent diameter less than about 10 microns). A suitable blending means is a twin screw extruder (e.g., the Polylab Twin Screw Extruder (available from Thermo Electron (Karlsruhe), Karlsruhe, Germany)) as are known to the art. Multicomponent polymer blend morphologies are typically dependent upon many factors such as the relative fraction and the melt rheology of each of component, their relative viscosity, as well as the compatibility of the various plastic and elastic components. For example, finer blend morphologies may be achieved between polymers having a greater thermodynamic affinity.

Suitable plasto-elastic compositions may comprise from about 95% to about 5%, by weight, of the elastic component, and preferably from about 90% to about 40%, by weight, of the elastic component. Preferably, the plasto-elastic compositions may comprise from about 5% to about 95%, and more preferably from about 10% to about 60%, by weight, of the plastic component. In some embodiments, the plasto-elastic composition may comprise more than two major components (i.e. more than two components are used at a level that is greater than about 5%).

The combination may be either in the form of a polymeric blend or a polymeric mixture, depending upon the degree of miscibility of the elastic and plastic components. If the combination forms a blend, one component can form the continuous phase that encloses dispersed particles of the other component(s). Preferably, the plasto-elastic composition comprises an interpenetrating blend having a co-continuous morphology with both phases forming interpenetrating networks.

Importantly, the polyolefin-based materials comprising the plasto-elastic composition are chosen so as to exhibit a unique combination of the plastic characteristic of traditional high-crystallinity polyolefins and the elastic characteristic of traditional elastomers. More specifically, the materials are chosen so as to provide the following mechanical performance profile to the plasto-elastic composition:

a) A low-force plastic (i.e., "permanent") deformation in response to an initial deformation strain cycle at a temperature of about room temperature and extending up to and including a temperature at, or slightly greater than, normal body temperature. Suitably, the "permanent" deformation extends is at least about 30% of the overall applied strain, preferably at least about 50%, more preferably at least about 70%. The applied strain can be either uniaxial or multivector.

b) The pre-stretched material then exhibits substantially elastic behavior upon multiple subsequent deformation cycles with low set, high recovery and low force relaxation at temperatures up to and including body temperature, especially over the range of strain applied during the original deformation cycle.

A suitable plasto-elastic material will have:

a) A relative amount of permanent dissipative viscoplastic deformation ranging from 15% to 140% of the initial strain cycle, for maximum extension values ranging from 50 to 500%, at temperatures ranging from about 20° C. to about 100° C. and initial strain rates ranging from 0.01 to 2000 $s^{-1}$. Preferably, the material can be deformed without failure at strain rates between about 1 to 2000 $s^{-1}$, more preferably 50 and 2000 $s^{-1}$, still more preferably at strain rates between 1000 and 2000 $s^{-1}$.

b) A dimensional stability of the material following the first loading cycle upon exposure to a temperature of up to 60° C. characterized by less than 20% change in the macroscopic dimensions of the material as measured by the Dimensional Stability in Storage Conditions test described in the TEST METHODS section below.

c) A permanent set value of less than 15% upon an extension of the material by a subsequent loading to a strain of at least 30% (preferably 40% and even more preferably 50%). Preferably the set is less than 10% of the strain applied upon each subsequent strain cycle;

d) A percent force relaxation less than 70%, preferably less than 50% at 50% strain (i.e., 150% elongation), for periods of up to 10 hr and for temperatures up to 40° C.

Fibers/Nonwovens

It has also been found that fibers comprising the plasto-elastic compositions described herein and nonwoven materials provide advantageous features when used as a component of a disposable absorbent article. Such features include, but are not limited to selective adjustability to fit a variety of body shapes because the fiber/nonwoven material facilitates "permanent" adjustment of portions of an absorbent article via plastic deformation and, at the same time, the article can continue to conform to a wearer's body throughout a wide range of body motion via elastic extensibility and efficient material utilization because a nonwoven comprising fibers of a plasto-elastic material can be selectively stretched to form a predefined shape during the manufacturing process thus reducing the amount of material that is discarded as scrap.

The fibers may be of any suitable size, that is the fiber may have a diameter or equivalent diameter of from about 0.5 micron to about 200 microns. Fiber diameters or equivalent diameters between about 10 and about 40 microns are particularly preferred. Said another way, fibers incorporating the plasto-elastics of the present invention are suitably between about 1 and about 10 denier, preferably between about 1 and about 8 denier, more preferably between about 1 and about 5 denier.

In one embodiment, the fibers comprise bicomponent fibers for improved consolidation. Bicomponent fibers are typically used as a means of better dissociating intrinsic fiber characteristics and bonding performance, the latter being typically dominated by the sheath in the case of bicomponent fibers. As is well known, a bicomponent fiber comprises first and second polymeric components that are coextruded so as to provide the fiber with certain desirable properties from each of the polymeric components (As will be recognized both the first and second polymeric components comprise thermoplastic polymers). For example a bicomponent fiber can comprise a first polymeric component having a lower softening temperature than the second polymeric component. Such structures reduce the risk of "burn through" during thermal consolidation.

The bicomponent fiber may be of any suitable configuration. Exemplary configurations include but are not limited to sheath-core, island-in-the sea, side-by-side, segmented pie and combinations thereof. In one optional embodiment of the present invention the bicomponent fibers have a sheath-core configuration.

Spunbond structures, staple fibers, hollow fibers and shaped fibers such as multi-lobal fibers can all be produced which comprise the plasto-elastics and mixtures of the present invention. The fibers of the present invention may have different geometries that include round, elliptical, star shaped, rectangular, and other various eccentricities.

The bicomponent fibers have a size comparable to those comprising only the plasto-elastic or mixture of the present invention. That is the fiber may have a diameter or equivalent diameter of from about 0.5 micron to about 200 microns. Fiber diameters or equivalent diameters between about 10 and about 40 microns are particularly preferred. Said another way, fibers incorporating the plasto-elastics of the present invention are suitably between about 1 and about 10 denier, preferably between about 1 and about 5 denier, more preferably between about 1 and about 3 denier.

As noted above, the bicomponent fibers comprise a first polymeric component and a second polymeric component. In specific embodiments of the present invention the first polymeric component comprises the plasto-elastic materials discussed above and the second polymeric component may comprise either a polymeric material having substantially elastic properties or a polymeric material having substantially plastic properties. As will be recognized, such specific embodiments can be tailored to have wide variety of mechanical properties depending on the particular combination of materials that is chosen.

The amount of first polymeric component and second polymeric component present in the bicomponent fiber will depend upon many factors, such as but not limited to, polymers present, desired use of bicomponent fiber, desired properties of the bicomponent fiber, etc. In one optional embodiment the weight ratio of the first polymeric component to the second polymeric component is from about 1:20 to about 20:1.

Typically, the fibers described above are consolidated into a nonwoven material. Consolidation can be achieved by methods that apply heat and/or pressure to the fibrous web, such as thermal spot (i.e., point) bonding. Thermal point bonding can be accomplished by passing the fibrous web through a pressure nip formed by two rolls, one of which is heated and contains a plurality of raised points on its surface, as is described in U.S. Pat. No. 3,855,046. Consolidation methods can also include, but are not limited to, ultrasonic bonding, through-air bonding, resin bonding, and hydroentanglement. Hydroentanglement typically involves treatment of the fibrous web with high pressure water jets to consolidate the web via mechanical fiber entanglement (friction) in the region desired to be consolidated, with the sites being formed in the area of fiber entanglement. The fibers can be hydroentangled as taught in U.S. Pat. Nos. 4,021,284 and 4,024,612.

Once consolidated, the web can be further processed (i.e., converted). For example, the web, either alone or in the form of a laminate with another material can be further processed to impart stretchability thereto. Methods for imparting stretchability to an extensible or otherwise substantially inelastic material by using corrugated interengaging rolls which incrementally stretch in the machine or cross-machine direction and permanently deform the material are disclosed in U.S. Pat. No. 4,116,892, U.S. Pat. No. 4,834,741, U.S. Pat. No. 5,143,679, U.S. Pat. No. 5,156,793, U.S. Pat. No. 5,167,897, U.S. Pat. No. 5,422,172, and U.S. Pat. No. 5,518,801. In some embodiments, the intermediate structure may be fed into the corrugated interengaging rolls at an angle with respect to the machine direction of this secondary operation. Alternatively, the secondary operation may employ a pair of interengaging grooved plates applied to the intermediate structure under pressure to achieve incremental stretching of the intermediate structure in localized portions. As noted above, the nonwoven webs of the present invention are particular suitable for these and similar processes because of their particularly desirable cold extensibility.

Nonwoven materials comprising the plasto-elastic materials of the present invention are particularly useful as a component of a disposable absorbent article (e.g., as a topsheet, a cuff material, a core wrap, and when laminated to a film or, otherwise, treated to be substantially impermeable to aqueous liquids as a backsheet). Although the nonwoven web of the present invention can find beneficial use as a component of a disposable absorbent article, such as but not limited to, disposable diapers, disposable incontinence briefs, disposable training pants, disposable pads or sheets for floor cleaning systems, such as the SWIFFER® cleaning system manufactured by The Procter & Gamble Company, catamenial products, disposable wipes, and the like; its use is not limited to disposable absorbent articles. The nonwoven web of the present invention can be used in any application requiring, or benefiting from a combination of elasticity and durable extensibility.

Films

In other embodiments, the plasto-elastic materials of the present invention may be advantageously employed in the extrusion of films. Such films may be produced using known processes such as casting. The plasto-elastic material may also be extrusion coated onto a nonwoven substrate effectively forming a film layer thereon.

Films comprising the plasto-elastic materials of the present invention may be monolithic (i.e. comprising only the plasto-elastic material). Alternatively, the plasto-elastic material may comprise a layer of a coextruded film. As will be recognized, such coextruded films may further include layers comprising other materials such as materials having substantially elastic properties or materials having substantially plastic properties.

Films according to the present invention find utility as components of absorbent articles. For example, such a film could provide liquid impermeability to a backsheet while also providing the capability to shape the backsheet. Alternatively such film may also be used to provide elastomeric contractions to, for example, a side panel of a disposable absorbent article. In this embodiment the plasto-elastic film provides initial adjustability to a particular body configuration via shaping strain cycle an then conformity to the body during wear due to its elastic property.

For end uses such as absorbent articles, such films should be thin and flexible. Desirably, a film comprising the plasto-elastic materials of the present invention has a caliper less than about 200 microns, preferably less than about 100 microns, more preferably less than about 50 microns. In order to have suitable durability, particularly during the manufacturing process, a film according to the present invention should have a caliper greater than about 10 microns.

Film basis weight is suitably greater than about 10 g/m$^2$, preferably greater than about 15 g/m$^2$. Desirably, films for use as a backsheet material have a basis weight between about 15 g/m$^2$ and about 35 g/m$^2$. As will be recognized, films used in other absorbent article components have different desirable ranges of basis weight. For example, films for use in a side panel desirably have a basis weight between about 40 g/m$^2$ and about 80 g/m$^2$.

Substrate

In certain embodiments of the present invention, the web materials described herein may be laminated to a substrate. Laminates may be combined by any number of bonding methods known to those skilled in the art including, but not limited to, thermal bonding, adhesive bonding including, but not limited to spray adhesives, hot melt adhesives, latex based adhesives and the like, sonic and ultrasonic bonding, and extrusion laminating whereby a polymer is cast directly onto another nonwoven, and while still in a partially molten state, bonds to one side of the nonwoven, or by depositing melt blown fiber nonwoven directly onto a nonwoven. These and other suitable methods for making laminates are described in U.S. Pat. No. 6,013,151 and U.S. Pat. No. 5,932,497.

Suitable substrate materials include but are not limited to: films, apertured films, foams, knitted fabric, woven fibrous webs or nonwoven fibrous webs as are known in the art. In some embodiments, the substrates are extensible nonwoven webs made of polyolefin fibers or filaments, such as polyethylene, or polypropylene. The substrate material may be elastic or inelastic, extensible or inextensible, stretchable or non-stretchable. Preferred substrates have a 3-dimensional morphology (i.e., via spacing between fibers, projections, holes, etc.) that facilitates the penetration of the thermoplastic elastomer into the substrate as described below.

Such substrate materials may suitably be formed from polymeric resins having either substantially elastic properties or substantially plastic properties so as to provide the substrate material with similar properties. As will be recognized, a laminate comprising a plasto-elastic web according to the present invention with a substrate having predefined stress/strain properties as may be chosen by a designer of absorbent articles gives the designer a wide range of options to meet particular design requirements.

In some embodiments the substrate cooperates with the plasto-elastic material to provide a limit to how much the plasto-elastic material may be strained during an initial strain cycle. Such limits can be advantageous, for example, when the plasto-elastic material is intended to provide a degree of size adjustability to a feature of an absorbent article where it would be undesirable for the extent strain cycle to be over large (e.g., preventing stretching a waistband so it is larger than the circumference of a wearer's waist). Such a limitation could be provided, for example, by disposing the plasto-elastic material onto the substrate while the substrate is in a shirred condition or by providing a substrate that is elastic in and of itself so that it provides a tactile signal of increasing strain to a caregiver. Suitably, a substrate of this type limits the initial strain cycle initial strain cycle such that the initial strain cycle elongates the plasto-elastic material no more than 100%. Optionally, the substrate limits the initial strain cycle such that the initial strain cycle elongates the plasto-elastic material no more than 75%.

Converting Processes

The web materials of the present invention are suitable for most typical converting processes used in the production of an absorbent article. Such processes include, but are not limited to neck bonding and stretch bonding as described above. The web materials may also be used to produce SELF materials as described in U.S. Pat. No. 5,691,035 and to produce zero strain stretch laminates as described in U.S. Pat. No. 5,156,793. When the web materials of the present invention are stretched in a converting process they may be stretched either uniaxially or along more than one axis (e.g. biaxially). The process of shaping the material into a form different than the original one can take place in several independent steps. The plasto-elastic web also may be printed, extrusion coated or adhesively attached to other webs using known processes to form laminated structures with plasto-elastic properties. It is immaterial whether such other webs are elastic or plastic, films or nonwovens.

EXAMPLES

Comparative Example 1

This example describes film formation from two resins of the prior art: an experimental grade of ADFLEX 7573 (a reactor blend of an ethylene-based elastomer and polypropylene available from Basell Polyolefins of Wilmington, Del.) (1-1); an isotactic polypropylene with stereoerrors along the polymer chain as disclosed in U.S. Pat. No. 6,555,643 (1-2); a high-performance blend typically used in diaper stretch components comprising a styrenic block copolymer available from Kuraray Co. Ltd. of Tokyo, Japan as Septon 4033 (1-3); an elastomeric polypropylene as is available from Exxon Mobil Chemical of Huston, Tex. as VISTAMAXX 1100 (1-4); and two blends of a very low density polyethylene (EXACT 4049 from Exxon Mobil of Huston, Tex.) and a linear low density polyethylene (LL6201 from Exxon Mobile Chemical of Huston, Tex.) where ID 1-5 is 85% VLDPE/15% LLDPE and 1-6 is 70% VLDPE/30% LLDPE. Tables 1 and 2 list film properties.

TABLE 1

| Composition ID | Prestrain Temperature (° C.) | Specimen width (mm) | Film basis weight (g/m$^2$) | Initial load @ 50% strain[1] (N) | Final load @ 50% strain[1] (N) | Force Relax.(10 hrs) (%) |
| --- | --- | --- | --- | --- | --- | --- |
| 1-1 | 23 | 12.7 | 97 | 3.44 | 1.49 | 57 |
| 1-2 | 23 | 12.7 | 141 | 1.06 | 0.54 | 49 |
| 1-3 | 23 | 15.9 | 179 | 0.61 | 0.44 | 28 |

TABLE 1-continued

| Composition ID | Prestrain Temperature (° C.) | Specimen width (mm) | Film basis weight (g/m²) | Initial load @ 50% strain[1] (N) | Final load @ 50% strain[1] (N) | Force Relax.(10 hrs) (%) |
|---|---|---|---|---|---|---|
| 1-4 | 23 | 19.0 | 151 | 0.99 | 0.40 | 59 |
| 1-5 | 23 | 12.7 | 143 | 2.27 | 0.98 | 57 |
| 1-6 | 23 | 12.7 | 103 | 2.24 | 1.14 | 49 |

[1]Normalized to 150 g/m² and 6.4 mm width

TABLE 2a

| | | 1st Cycle (200%, RT) | | | 2nd Cycle (50%, R.T.) | | |
|---|---|---|---|---|---|---|---|
| Blend ID | Basis Weight g/m² | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 1-1 | 111 | 6.88 | 87.9 | 6.36 | 51.4 | 0.25 | 15.3 |
| 1-2 | 154 | 2.74 | 3.9 | 1.24 | 18.8 | 0.64 | 6.7 |
| 1-3 | 128 | 1.13 | 5.4 | 0.64 | 7.5 | 0.39 | 4.0 |
| 1-4 | 148 | 1.75 | 13.6 | 0.95 | 17.4 | 0.45 | 6.7 |

TABLE 2b

| | | 1st Cycle (300%, RT) | | | 2nd Cycle (200%, R.T.) | | |
|---|---|---|---|---|---|---|---|
| Blend ID | Basis Weight | Stress @ 200% Prestrain | % Set after 1st Cycle | Stress @ 50% | % Force Relaxation @ 50% | Stress @ 30% Unload | % Set after 2nd Cycle |
| 1-5 | 180 | 3.54 | 74.2 | 4.15 | 29.8 | * | >30% |
| 1-6 | 168 | 4.14 | 86.5 | 5.12 | 32.0 | * | >30% |

* Stress too low to measure

As can be seen: 1) the polyethylene-containing blends typically have a relatively high stress at both 200% and 50% elongations (related to stiffness), 2) a high force relaxation after a second elongation cycle (>15%) and, sometimes, 3) negligible stress at 30% elongation during the unload of the second cycle and/or a high level of additional set after a second loading cycle.

Example 2

This example illustrates the properties of blends of two different elastomeric polyolefins.

The blends shown in Table 3 were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation.

TABLE 3

| Composition ID | Elastomeric Isotactic Polypropylene[1] | Elastomeric Polypropylene[2] | Very Low Density Polyethylene[3] | Styrenic Blend[4] | Reactor Polypropylene Copolymer[5] |
|---|---|---|---|---|---|
| 2-1 | | 40 | | | 60 |
| 2-2 | | 60 | | | 40 |
| 2-3 | 20 | | | | 80 |
| 2-4 | 40 | | | | 60 |
| 2-5 | | | 20 | | 80 |
| 2-6 | | | 40 | | 60 |
| 2-7 | | 85 | | | 15 |

[1]Isotactic polypropylene with stereoerrors along the polymer chain as disclosed in U.S. Pat. No. 6,555,643
[2]VISTAMAXX 1100 as is available from Exxon Mobil Chemical of Huston, TX.
[3]Exact 4049 is avialable from Exxon Mobil Chemical of Huston, TX.
[4]High-performance blnd typically used in diaper stretch components comprising a styrenic block copolymer available from Kuraray Co. Ltd. of Tokyo, Japan as Septon 4033
[5]Soft polypropylene-based thermoplastic elastomer reactor blend produced using Catalloy technology and available as ADFLEX 7353 from Basell Polyolefins of Elkton, MD.

Properties of the films are shown in Tables 4 and 5.

Compression-molded films were prepared with a Carver press (Available from Carver, Inc. of Wabash, Ind.) using the following steps:
1. Place a Teflon® template (A Teflon® sheet with the center area cut away to define the sample area). The thickness of the sheet determines the thickness of the sample.) on a 0.005" thick Teflon® sheet. Place composition to be formed onto the press, in the open area of the template. Cover with a second 0.005" thick Teflon® sheet.
2. Place the Teflon® sheets/composition "sandwich" between heated (200° C.) platens of the Carver Press and slowly load to 5,000 pounds of pressure. Wait 30 seconds.
3. Increase pressure to 12,000 lbs and wait 60 seconds.
4. Release pressure, rotate the Teflon® sheets/composition "sandwich" 180° and load to 12,000 lbs. Wait 30 seconds and release pressure.
5. Immediately remove the Teflon® sheets/composition "sandwich" and cool it between room-temperature metal plates.
6. If the film that has been formed does not readily release from the Teflon®, place in a freezer, wait 5 minutes, and peel film from Teflon®.

The film samples were allowed to age for 24 hrs before being subjected to mechanical testing.

TABLE 4

| Comp. ID | Prestrain Temperature[1] (° C.) | Specimen Width (mm) | Film Basis Weight (g/m$^2$) | Initial Load @ 50% Strain[2] (N) | Final Load @ 50% Strain[2] (N) | Force Relax.(10 hrs) (%) |
|---|---|---|---|---|---|---|
| 2-1 | 23 | 19.1 | 109 | 0.73 | 0.35 | 53 |
| 2-2 | 23 | 12.7 | 149 | 0.69 | 0.26 | 61 |
| 2-3 | 23 | ⅜ | 161 | 0.67 | 0.35 | 46 |
| 2-4 | 23 | ½ | 159 | 0.68 | 0.37 | 46 |
| 2-5 | 23 | ½ | 149 | 0.68 | 0.38 | 44 |
| 2-6 | 23 | ½ | 197 | 0.83 | 0.45 | 46 |
| 2-7 | 23 | 19.1 | 106 | 1.18 | 0.66 | 43 |

[1]Temperature at which prestrain and relaxation steps were conducted.
[2]Normalized to 150 g/m$^2$ and 6.4 mm width

TABLE 5

| Composition ID | Basis Weight (g/m$^2$) | 1st Cycle (200%, RT) | | | 2nd Cycle (50%, R.T.) | | |
|---|---|---|---|---|---|---|---|
| | | Stress @ 200% Prestrain (MPa) | Set after 1st Cycle (%) | Stress @ 50% (MPa) | Force Relaxation @ 50% (%) | Stress @ 30% Unload (MPa) | |
| 2-1 | 167 | 2.12 | 14.4 | 1.29 | 9.3 | 0.41 |
| 2-2 | 150 | 1.80 | 16.5 | 1.15 | 12.0 | 0.31 |
| 2-3 | 173 | 2.54 | 13.8 | 1.37 | 8.3 | 0.45 |
| 2-4 | 186 | 2.47 | 16.7 | 1.45 | 12.7 | 0.36 |
| 2-5 | 172 | 1.95 | 14.9 | 1.33 | 8.4 | 0.39 |
| 2-6 | 187 | 2.38 | 19.8 | 1.65 | 13.0 | 0.37 |
| 2-7 | 126 | 3.13 | 24.2 | 2.36 | 24.7 | 0.35 |

The hysteresis and force data suggest a possible synergy that results from combining elastomers. For example, styrenic elastomers are known to exhibit low force relaxation over short periods of time but, over longer periods of time relaxation becomes significant. Conversely, elastomeric polyolefins demonstrate more rapid force relaxation over short time periods but relaxation stabilizes over longer periods of time. As can be seen in this example, blends of these elastomers have been found to provide a more progressive decline in force relaxation with time. In an absorbent article context, this progressive decline provides a meaningful benefit by minimizing redmarking in the short term (lower initial contractive forces are required because force does not decline substantially with time) while providing less reduction in contractive force over long time periods.

Example 3

This example illustrates the possibility of modifying the tensile properties of a commercial elastomeric polypropylene via the addition of a commercial soft, deformable polyolefin-based material.

The following materials were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation. The following compositions (all values in wt. percent) were prepared according Table 6

TABLE 6

| Composition ID | Elastomeric Polypropylene[1] | Polyolefin Material[2] | LLDPE[3] | VLDPE[4] |
|---|---|---|---|---|
| 3-1 | 100 | 0 | 0 | 0 |
| 3-2 | 60 | 40 | 0 | 0 |
| 3-3 | 60 | 30 | 10 | 0 |
| 3-4 | 60 | 30 | 0 | 10 |
| 3-5 | 40 | 60 | 0 | 0 |

TABLE 6-continued

| Composition ID | Elastomeric Polypropylene[1] | Polyolefin Material[2] | LLDPE[3] | VLDPE[4] |
|---|---|---|---|---|
| 3-6 | 40 | 45 | 15 | 0 |
| 3-7 | 40 | 45 | 0 | 15 |

[1]Elastomeric polypropylene as is available from Exxon Mobil Chemical of Huston, TX as VISTAMAXX 1100.
[2]PARAFILM M is a polyolefin laboratory film commercialized by American National Can of Chicago, IL. The film was cut into pieces prior to being added to the batch mixer.
[3]Linear low Density polyethylene (MI = 50 g/10 min, Density = 0.926 g/cm$^3$,) as is available from Exxon Mobil Chemical of Huston, TX as LL6201.
[4]Very low density polyethylene (MI = 4.5 g/10 min; Density = 0,873 g/cm$^3$) as is available from Exxon Mobil Chemical of Huston, TX as EXACT 4049.

Compression-molded films were prepared with a Carver press using the method described in Example 2. Force relaxation (Table 7) and hysteresis testing (Tables 8 and 9) was carried out according to the methods described above and the data are shown in the following tables (A minimum of two specimens was analyzed for each reported value):

TABLE 7

| Composition ID | Prestrain Temperature[1,2] (° C.) | Specimen Width (mm) | Film Basis Weight (g/m$^2$) | Initial Load @ 50% Strain[3,4] (N) | Final Load @ 50% Strain[3,4] (N) | Force Relax.(10 hrs) (%) |
|---|---|---|---|---|---|---|
| 3-1 | 23 | 19 | 151 | 0.99 | 0.40 | 59 |
| 3-2 | 23 | 19 | 131 | 0.82 | 0.23 | 71 |
| 3-2 | 40 | 19 | 120 | 0.54 | 0.19 | 65 |
| 3-2 | 40[3] | 13 | 135 | 0.48 | 0.16 | 66 |
| 3-3 | 23 | 19 | 104 | 0.87 | 0.25 | 70 |
| 3-4 | 23 | 13 | 124 | 0.89 | 0.26 | 71 |
| 3-5 | 23 | 19 | 109 | 0.58 | 0.14 | 77 |
| 3-5 | 40 | 13 | 97 | 0.46 | 0.14 | 70 |
| 3-6 | 23 | 19 | 106 | 1.05 | 0.33 | 69 |
| 3-7 | 23 | 13 | 104 | 1.09 | 0.35 | 68 |

[1]Temperature at which prestrain step was conducted.
[2]Prestrained to 300% instead of 200%
[3]Normalized to 150 g/m$^2$ and 6.4 mm width
[4]Strained to 50% before reaching temperature equilibrium in environmental chamber

TABLE 8

| | | 1st Cycle (200%, RT) | | | 2nd Cycle (50%, R.T.) | | |
|---|---|---|---|---|---|---|---|
| Composition ID | Basis Weight (g/m$^2$) | Stress @ 200% Prestrain (MPa) | Set after 1st Cycle (%) | Stress @ 50% (MPa) | % Force Relaxation @ 50% (%) | Stress @ 30% Unload (MPa) | % Set after 2nd Cycle % |
| 3-1 | 148 | 1.75 | 13.6 | 0.95 | 17.4 | 0.45 | 6.7 |
| 3-2 | 156 | 1.45 | 30.1 | 0.84 | 26.7 | 0.21 | 7.8 |
| 3-3 | 106 | 2.12 | 24.4 | 1.00 | 26.4 | 0.25 | 7.9 |
| 3-4 | 135 | 2.04 | 22.4 | 1.02 | 24.5 | 0.31 | 7.6 |
| 3-5 | 117 | 1.25 | 43.4 | 0.81 | 31.7 | 0.13 | 9.6 |
| 3-6 | 104 | 2.29 | 48.1 | 0.60 | 34.7 | 0.08 | 10.0 |
| 3-7 | 110 | 2.50 | 46.6 | 1.34 | 24.5 | 0.26 | 7.9 |

TABLE 9[1]

| | | 1st Cycle (300%, RT) | | | 2nd Cycle (200%, R.T.) | |
|---|---|---|---|---|---|---|
| Composition ID | Basis Weight g/m$^2$ | Stress @ 300% Prestrain MPa | Set after 1st Cycle % | Stress @ 200% MPa | Force Relaxation @ 200% % | |
| 3-1 | 132 | 1.92 | 19.6 | 1.50 | 18.3 | |
| 3-2 | 161 | 1.69 | 46.5 | 1.82 | 32.7 | |
| 3-3 | 108 | 2.55 | 36.8 | 2.26 | 31.7 | |
| 3-4 | 134 | 2.53 | 37.6 | 2.36 | 28.8 | |
| 3-5 | 130 | 1.40 | 74.4 | 1.80 | 38.9 | |
| 3-6 | 112 | 2.37 | 83.5 | 2.80 | 41.4 | |
| 3-7 | 112 | 2.76 | 78.4 | 3.37 | 35.1 | |

[1]Modified hysteresis test (initial 300% cycle, followed by 2$^{nd}$ 200% cycle (hold for 30 sec at 200%))

As can be seen, blending PARAFILM M into VISTAMAXX results in large % set values in the film as a result of pre-straining; The higher the strain, the higher the set (>80% set for a blend containing 60% PARAFILM strained up to 300% at room temperature). It is believed that the PARAFILM M lowers the stress required to deform the material up to a given strain, whether during the initial cycle or at low strains in subsequent cycles. Said another way, it provides the plasto-elastic functionality with as soft touch and feel that nicely complement the conforming fit benefit from the VISTAMAXX. As can be seen, Adding a linear low density polyethylene component (with more or less crystallinity) to the blends tends to increase both loading and loading stresses, without much influence on the amount of set and/or force relaxation. The % force relaxation at body temperature after 10 hrs increases with the addition of PARAFILM, an indication of a partial loss in the elastic/recoverable characteristics of the material.

Table 10 illustrates the amount of permanent deformation (expressed in terms of specimen length relative to initial sample length) for the above material compositions when subjected to 2 successive deformation cycles up to 300% or 500% (of the original sample length in both deformations) at room temperature (~23° C.). Compression-molded film samples were used having 5 mm width and 2 cm length. The samples were hand-strained to a first stretch dimension (i.e. 300% for 3-1, 500% for the plasto-elastic compositions 3-2 to 3-7), held for 3 sec and allowed to relax for 5 min before the operation was repeated.

TABLE 10

| Composition ID | Initial Dimension (cm; %) | First Stretch Dimension (cm; %) | First Relaxed Dimension (cm; %) | Second Stretch Dimension (cm; %) | Second Relaxed Dimension (cm; %) |
|---|---|---|---|---|---|
| 3-1 | 2; 100% | 6; 300% | 2.3; 115% | 6; 300% | 2.3; 115% |
| 3-2 | 2; 100% | 10; 500% | 3.1; 155% | 10; 500% | 3.15; 158% |
| 3-3 | 2; 100% | 10; 500% | 3.1; 155% | 10; 500% | 3.2; 160% |
| 3-4 | 2; 100% | 10; 500% | 3.0; 150% | 10; 500% | 3.15; 158% |
| 3-5 | 2; 100% | 10; 500% | 3.7; 185% | 10; 500% | 3.85; 193% |
| 3-6 | 2; 100% | 10; 500% | 4.5; 225% | 10; 500% | 4.65; 233% |
| 3-7 | 2; 100% | 10; 500% | 4.6; 230% | 10; 500% | 4.75; 238% |

As can be seen, the plasto-elastic blends (3-2 to 3-7) exhibit an increase in permanent size in the range of 50% to 125% as the result of the incorporation of various amounts of PARAFILM. The addition of LLDPE or VLDPE to PARAFILM further enhances the % set in blends when PARAFILM is the majority component of the blend. It should also be noted that set does not substantially increase on an additional strain cycle. For example, the difference in % set between the first and second cycle is typically less than 10% and often less than 5%. This is an indication of the excellent dimensional stability of the plasto-elastic composition beyond the prestraining cycle. Said another way, there is substantially elastic behavior after the first prestraining cycle.

Example 4

This example illustrates the effect on a variety of elastomeric materials due to the addition of a commercial soft, deformable polyolefin-based material (PARAFILM M).

The following materials were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation. Table 11 describes the compositions that were prepared (all values in wt. percent).

TABLE 11

| Composition ID | Polyolefin Material[1] | Styrenic Block Copolymer Blend[2] | Very Low Density Polyethylene[3] | Linear Low Density Polyethylene[4] | VLDPP[5] | Metallocene Polypropylene[6] |
|---|---|---|---|---|---|---|
| 4-1 | 40 | 60 | | | | |
| 4-2 | 60 | 40 | | | | |
| 4-3 | 40 | | 51 | 9 | | |
| 4-4 | 60 | | 34 | 6 | | |
| 4-5 | 40 | | | | 51 | 9 |
| 4-6 | 60 | | | | 34 | 6 |
| 4-7 | 50 | 30 | 17 | 3 | | |
| 4-8 | 50 | 30 | | | 17 | 3 |
| 4-9 | 50 | 25 | | | 21.25 | 3.75 |

[1] PARAFILM M is a polyolefin laboratory film commercialized by American National Can of Chicago, IL. The film was cut into pieces prior to being added to the batch mixer.

[2] A high-performance blend typically used in diaper stretch components. It consists of a Styrenic Block Copolymer available from Kuraray Co. Ltd. of Tokyo, Japan as Septon 4033, a polystyrene grade from Nova Chemicals of Pittsburgh, PA as PS3190 and an oil available from Penreco of The Woodlands, TX as Drakeol 600 that are blended together at a 55/10/35 ratio.

[3] EXACT 4049 (MI = 4.5 g/10 min; Density = 0.873 g/cm$^3$) available from Exxon Mobil Chemical Co of Huston, TX.

[4] LL6201 (MI = 50 g/10 min, Density = 0.926 g/cm$^3$,) available from Exxon Mobil Chemical Co of Huston, TX.

[5] VLDPP MARS 3900 (MFR ~3 g/10 min; density = 0.862 g/cm$^3$) is a very low density polypropylene material that is described in U.S. Pat. No. 6,555,643.

[6] A metallocene polypropylene (MFR = 8 g/10 min; Density = 0.950 g/cm$^3$) as is available from Atofina Petrochemicals of Huston, TX as EOD-00-07.

Note that in the case of the very low crystallinity polyolefin materials, a small fraction (up to about 15% in the composition created above) of a higher crystallinity material may be added Compression-molded films were prepared with a Carver press using the method described in Example 2. Force relaxation (Table 12) and hysteresis testing (Table 13) was carried out according to the methods described above and the data are shown in the following tables (A minimum of two specimens was analyzed for each reported value):

TABLE 12

| Composition ID | Pre-strain Temperature (° C.) | Specimen Width (mm) | Film Basis weight (g/m²) | Initial load @ 50% strain[1,2] (N) | Final load @ 50% strain[1,2] (N) | Force Relax. after 10 hrs (%) |
|---|---|---|---|---|---|---|
| 4-1 | 23 | 13 | 118 | 0.57 | 0.23 | 60 |
| 4-2 | 23 | 13 | 152 | 0.63 | 0.22 | 66 |
| 4-3 | 23 | ¼ | 118 | 2.68 | 1.08 | 60 |
| 4-4 | 23 | 13 | 144 | 2.19 | 0.80 | 63 |
| 4-5 | 23 | 13 | 133 | 0.99 | 0.31 | 68 |
| 4-6 | 23 | 25 | 108 | 0.84 | 0.25 | 70 |
| 4-7 | 23 | 13 | 140 | 1.23 | 0.51 | 59 |
| 4-8 | 23 | 13 | 130 | 0.74 | 0.30 | 60 |
| 4-9 | 23 | 13 | 124 | 0.78 | 0.23 | 71 |

[1]Normalized to 150 g/m² and 6.4 mm width
[2]Strained to 50% before reaching temperature equilibrium in environmental chamber

TABLE 13

| | | 1st Cycle (200%, RT) | | | 2nd Cycle (50%, R.T.) | | |
|---|---|---|---|---|---|---|---|
| Composition ID | Basis Weight g/m² | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 4-1 | 137 | 1.71 | 15 | 0.82 | 17.2 | 0.35 | 7.2 |
| 4-2 | 114 | 1.21 | 30 | 0.53 | 26.5 | 0.13 | 8.5 |
| 4-3 | 125 | 4.03 | 89 | 3.69 | 25.4 | 0.60 | 10.0 |
| 4-4 | 139 | 3.61 | 98 | 3.44 | 28.3 | 0.40 | 12.4 |
| 4-5 | 143 | 2.60 | 41 | 1.24 | 36.8 | 0.15 | 8.0 |
| 4-6 | 123 | 2.04 | 67 | 1.26 | 43.2 | 0.04 | 12.5 |
| 4-7 | 133 | 2.21 | 64 | 1.50 | 23.9 | 0.35 | 8.3 |
| 4-8 | 138 | 1.78 | 31 | 0.82 | 29.7 | 0.17 | 7.4 |
| 4-9 | 137 | 1.59 | 38.5 | 0.82 | 31.8 | 0.13 | 9.9 |

As can be seen, adding PARAFILM M results in large % set values in the film during prestraining for a variety of elastomeric materials. At comparable PARAFILM/elastomer blend compositions, the styrene block copolymer-based blend exhibits the least amount of set as well as the lowest amount of force relaxation, whether the latter is measured at room temperature after 30 sec or after 10 hrs at body temperature. Normalized load values also remain relatively low. The elastomeric polypropylene-based grades (Blends 2 and 5 of Example 3) exhibit higher set values, somewhat higher force relaxation as well as slightly higher load values. The elastomeric polyethylene blends exhibit the highest % set values (large shaping component), high load values and relatively low force. Also, tri-component blends that combine PARAFILM with two different types of elastomers (as illustrated by compositions 4-7 to 4-9) may be created to further tailor the balance of properties of the blend to those required for any specific application.

Example 5

This example illustrates the effect on tensile properties of a commercial elastomeric polypropylene grade (VISTAMAXX) by the addition of wax/polyolefin mixtures.

The following blends were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation. Compositions according Table 14 were prepared (values expressed in weight %).

TABLE 14

| Composition ID | Elastomeric PP | | | Blend Component | | | | |
| --- | --- | --- | --- | --- | --- | --- | --- | --- |
| | Polypropylene Random Copolymer[1] | Reactor Blend Polypropylene[2] | Linear Low Density Polyethylene[3] | Microcrystalline Wax[4] | Low Molecular Weight Polyethylene/Wax[5] | Low Molecular Weight Polyethylene[6] | Polypropylene Wax[7] | Very Low Molecular Weight Polyisobutylene[8] |
| 5-1 | 60 | | 8 | | 24 | | | 8 |
| 5-2 | 60 | | 8 | | 32 | | | |
| 5-3 | 60 | | 8 | 32 | | | | |
| 5-4 | 50 | 10 | 8 | | 32 | | | |
| 5-5 | 40 | | 12 | | 48 | | | |
| 5-6 | 60 | | | | 20 | 20 | | |
| 5-7 | 60 | | 10 | | 10 | | 20 | |

[1] Available from Exxon Mobil Chemical of Huston, TX as VISTAMAXX 1100.
[2] Soft polypropylene-based thermoplastic elastomer reactor blend produced using Catalloy technology and available as ADFLEX 7353 from Basell Polyolefins of Elkton, MD.
[3] Linear low density polyethylene (Melt Index = 50 g/10 min, Density = 0.926 g/cm$^3$) as is available as LL6201 from Exxon Mobil Chemical Co of Huston, TX.
[4] Microcrystalline wax available from the Crompton Corporation of Middlebury, CT as MULTIWAX W-835.
[5] Refined Wax 128 is a low melting refined petroleum wax available from the Chevron Texaco Global Lubricants of San Ramon, CA.
[6] A low molecular weight polyethylene as is available for Honeywell Specialty wax and additives of Morristown, NJ as A-C 735.
[7] A low molecular weight polypropylene as is available from Clariant, Pigments & Additives Division of Coventry, RI as LICOWAX PP230.
[8] A very low molecular weight polyisobutylene as is available from BASF of Ludwigshafen, Germany as OPPANOL B.

Compression-molded films were prepared with a Carver press using the method described in Example 2. Force relaxation and hysteresis testing was carried out according to the methods described above and the data are shown in Tables 15 and 16 below (minimum of two specimens):

TABLE 15

| Composition ID | Prestrain Temperature (° C.) | Specimen Width (mm) | Film Basis Weight (g/m$^2$) | Initial load @ 50% Strain[1] (N) | Final load @ 50% Strain[1] (N) | Force Relaxation (%) |
| --- | --- | --- | --- | --- | --- | --- |
| 5-1 | 23 | 25 | 115 | 0.39 | 0.11 | 72 |
| 5-2 | 23 | 25 | 107 | 0.46 | 0.16 | 66 |
| 5-3 | 23 | 25 | 118 | 0.43 | 0.13 | 70 |
| 5-4 | 23 | 25 | 122 | 0.65 | 0.28 | 57 |
| 5-5 | 23 | 25 | 86 | 0.64 | 0.24 | 62 |
| 5-6 | 23 | 13 | 137 | 0.79 | 0.31 | 60 |
| 5-7 | 23 | 13 | 126 | 0.95 | 0.45 | 53 |

[1] Normalized to 150 g/m$^2$ and 6.4 mm width

TABLE 16

| Composition ID | Basis Weight g/m$^2$ | 1st Cycle (200%, RT) | | | 2nd Cycle (50%, R.T.) | |
| --- | --- | --- | --- | --- | --- | --- |
| | | Stress @ 200% Prestrain MPa | % Set after 1st Cycle % | Stress @ 50% MPa | % Force Relaxation @ 50% % | Stress @ 30% Unload MPa |
| 5-1 | 124 | 1.56 | 29.3 | 0.78 | 30.0 | 0.15 |
| 5-2 | 115 | 1.62 | 39.3 | 0.94 | 30.6 | 0.15 |
| 5-3 | 132 | 1.11 | 28.4 | 0.64 | 29.0 | 0.14 |
| 5-4 | 131 | 2.07 | 39.3 | 1.10 | 32.3 | 0.16 |
| 5-5 | 90 | 1.92 | 94.9 | 1.63 | 45.8 | 0 |
| 5-6 | 131 | 1.86 | 20.4 | 1.02 | 21.9 | 0.39 |
| 5-7 | 127 | 2.59 | 24.5 | 1.16 | 27.5 | 0.35 |

As can be seen, various combinations of high molecular weight polyethylene, molecular weight polyethylene, polyethylene wax and polypropylene wax can be blended with a polypropylene-based elastomer to provide a blend with a combination of plastic and elastic properties. Adding a fraction of reactor blend elastomeric polypropylene not only lowers the amount of force relaxation but also increases stress values.

Example 6

This example describes film formation from blends of an isotactic polypropylene with stereoerrors along the polymer chain as disclosed in U.S. Pat. No. 6,555,643 the isotactic polypropylene resin was blended with various modifiers as described in Table 17. Samples 6-1 to 6-5 were compounded (including commonly used stabilizer materials such as anti-oxidants and the like at <1% of the blend) using a laboratory-scale mixer available from C. W. Brabender Instruments of Hackensack, N.J. The films were compression molded into films having a thickness of ~200µ by heating to ~200° C. and compressing between PTFE sheets in a Carver Press using a method similar to steps 1 through 14 in the Hysteresis Test method described below.

TABLE 17

| Composition ID | Polymer According to U.S. Pat. No. 6,555,643 (%) | Modifier (%) |
|---|---|---|
| 6-1 | 100 | — |
| 6-2 | 85 | 15[a] |
| 6-3 | 70 | 30[1] |
| 6-4 | 55 | 45[1] |
| 6-5 | 70 | 30[2] |

[1]Experimental metallocene polypropylene having a melt flow rate of 8 grams/10 minutes from Ato-Fina Chemicals of Houston TX as code EOD 00-07
[2]Polypropylene-based nanoclay concentrate available from PolyOne of Arlington Heights, IL PolyOne 1001 master batch concentrate (50% clay).

The properties according to the Hysteresis Test for these blends are shown in Table 18.

TABLE 18

| Composition ID | Basis Weight g/m² | 1st Cycle (200%, RT) | | | 2nd Cycle (50%, R.T.) | | |
|---|---|---|---|---|---|---|---|
| | | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 6-1[1] | 154 | 2.74 | 3.9 | 1.24 | 18.8 | 0.64 | 6.7 |
| 6-2 | 185 | 3.49 | 17.8 | 1.81 | 28.3 | 0.60 | 5.0 |
| 6-3 | 192 | 6.93 | 34.8 | 3.04 | 42.2 | 0.28 | 11.3 |
| 6-4 | 167 | 8.91 | 76.0 | 7.51 | 55.2 | 0.19 | 12.0 |
| 6-5 | 167 | 7.15 | 30.7 | 2.80 | 43.7 | 0.30 | 8.2 |

[1]Data same as Blend 1-2

Example 7

This example demonstrates spinning of fibers from polyolefin elastomer blends and plasto-elastic blends according to the present invention. Fibers were spun from: 1) a random polypropylene copolymer resin (available from Exxon Mobil Chemical of Huston, Tex. as VISTAMAXX 1120) and 2) a plasto-elastic material according to the present invention (same composition as 5-7 of Example 5) using a two extruder system, where each extruder is a horizontal single-screw extruder. The extrudate rate from each extruder to the spinpack is controlled by a metering melt pump that feeds a 4-hole spin pack (Hills Incorporated, W. Melbourne, Fla.). Table 19 lists the extrusion conditions that were found to lead to successful fiber formation:

TABLE 19

| | | Extruder | |
|---|---|---|---|
| Extruder Condition | | 7-1 | 7-2 |
| Temperature Range | ° C. | 135-180 | 135-180 |
| Melt Temp. | ° C. | 185 | 185 |
| Melt Pressure | MPa | 10.3 | 10.3 |

TABLE 19-continued

| | | Extruder | |
|---|---|---|---|
| Extruder Condition | | 7-1 | 7-2 |
| Spinpack Melt Temp | ° C. | 200 | 195 |
| Spinpack Pressure | MPa | <21 | <21 |
| Mass Throughput | g/h/min | 0.3 | 0.3 |

Fibers were successfully spun using both of these materials at attenuating air pressures of up to 483 kPa (70 psi).

Example 8

This example is intended to demonstrate formation of a nonwoven web comprising the plasto-elastic material of the present invention.

A small web was produced using the 4-hole fiber spinning line described above. Bicomponent fibers (core=25% a random polypropylene copolymer (VISTAMAXX 2100 from Exxon Mobil Chemical of Huston, Tex.) and shell=75% of the plasto-elastic formulation 5-7) were spun using an attenuating air pressure of 40 psi. Spun fibers were first gathered on a small-scale moving table and bonded ultrasonically using a bonding device assembled by Machinetek of Fairfield, Ohio that incorporates a Branson 900 BCA Ultrasonic Probe (Branson Ultrasonic Corporation of Danbury, Conn.). The webs were bonded at a pressure of 276 KPa. The amplitude of the signal (dial position 50) and the speed of the web (dial position 8) defined ultrasonic energy and residence time respectively. Increased amplitude, higher pressure and smaller web speed all contribute to higher bonding The resulting nonwoven web had a basis weight of about 49.2 g/m².

Figure 1:
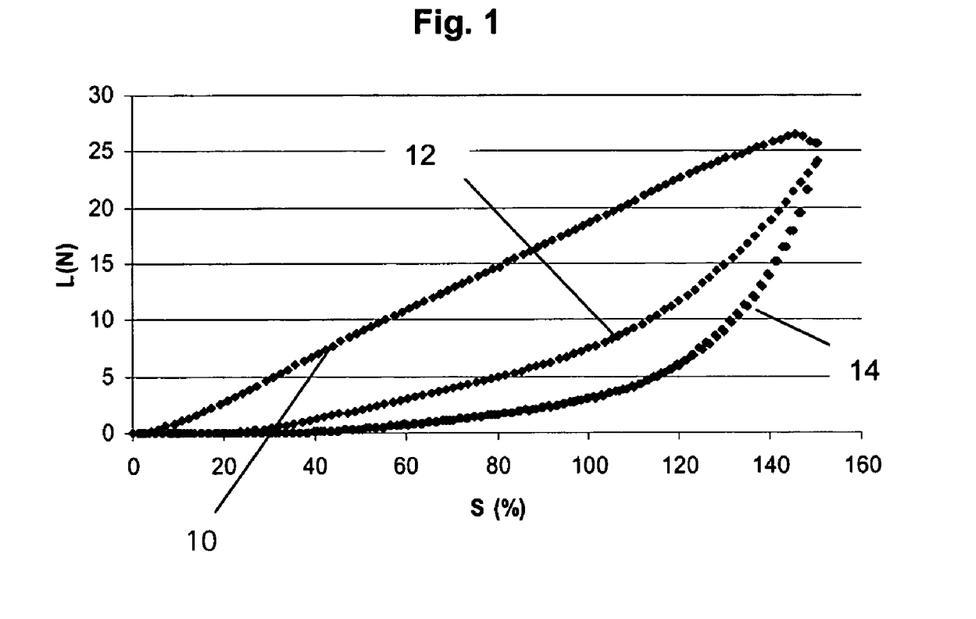
FIG. 1 is a graph of data from an hysteresis evaluation of a nonwoven material comprising the plasto-elastic materials of the present invention.

The results of a two cycle hysteresis evaluation of the web (extension to 150% at room temperature (~23° C.)) are shown in FIG. 1 where 10 is the extension portion of the first cycle, 14 is the return portion of both cycles (it should be noted that the web follows the same return path for both cycles) and 12 is the extension portion of the second cycle. In this figure load L in Newtons is plotted against percent elongation S. The percent set (~30%) due to the first extension cycle can be seen in the starting point of the second cycle. Additional cycles (not shown) indicate the web follows substantially the same curve as 12 on extension and 14 on return with only minimal (<15%) additional set.

Example 9

This example is intended to demonstrate formation of a film comprising the plasto-elastic material of the present invention.

The plasto-elastic formulation according to the present invention (Composition 5-7 from Example 5) was extruded into a film on a lab-scale Haake Polylab extrusion apparatus (available from Thermo Electron (Karlsruhe), Karlsruhe, Germany) with a flat die and take-off unit set up for a line speed of 21 m/min. The film was collected on a roll of release paper. The film had a caliper of about 76μ and width of about 11.4 cm.

Figure 2:
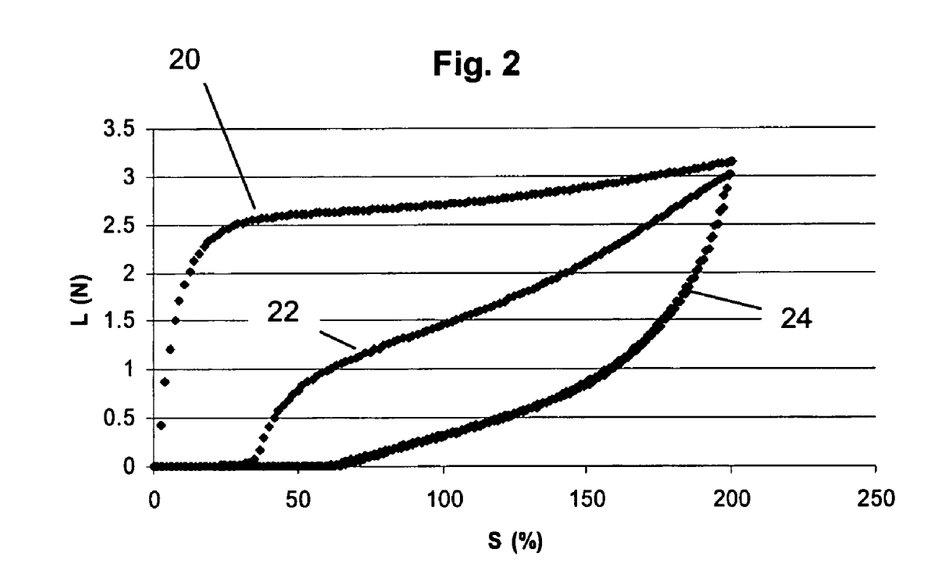
FIG. 2 is a graph of data from an hysteresis evaluation of an extruded film comprising the plasto-elastic materials of the present invention.

The results of a two cycle hysteresis evaluation of the film (extension to 200% at room temperature (~23° C.)) are shown in FIG. 2 where 20 is the extension portion of the first cycle, 24 is the return portion of both cycles (it should be noted that the web follows the same return path for both cycles) and 22 is the extension portion of the second cycle. In this figure load L in Newtons is plotted against percent elongation S. The percent set (~35%) due to the first extension cycle can be seen in the starting point of the second cycle. Additional cycles (not shown) indicate the film follows substantially the same curve as 12 on extension and 14 on return with only minimal (<15%) additional set.

TEST METHODS

Apparatus

Tensile Tester: A commercial constant rate of extension tensile tester from Instron Engineering Corp., Canton, Mass. or SINTECH-MTS Systems Corporation, Eden Prairie, Minn. (or a comparable tensile tester) may is suitable. The instrument is interfaced with a computer for controlling the test speed and other test parameters, and for collecting, calculating and reporting the data.

Load Cell Choose the jaws and load cell suitable for the test; the jaws should be wide enough to fit the sample, typically 2.54 cm jaws are used; the load cell is chosen so that the expected tensile response from the sample tested will be between 25% and 75% of the capacity of the load cells or the load range used, typically a 1 kN load cell is used;

Sample Cutter The specific sample cutter is defined by the desired sample width. Suitable cutters are available from Thwing-Albert Instrument Co. of Philadelphia, Pa.

For a 2.54 cm wide sample a Model JDC 1-10 is suitable.

Sample Preparation

The plasto-elastic material is first separated from any substrate or other material to which it is attached by any suitable means. One such means is to freeze the sample so as to reduce the bond strength between the plasto-elastic material and other materials. A suitable freezing medium is compressed 1,1,1,2 tetrafluoroethane sold under the trade name QUICK-FREEZE by Miller-Stephenson Chemical Company of Danbury, Conn.

Separate enough sample to prepare at least three specimens 2.5 cm×5 cm (~15 grams). The Specimens are prepared using the following method:

1) Weigh approximately 12 grams of the elastomeric composition of interest.
2) Compression mold the composition by placing the pre-weighed material between two pieces of 0.010 inch (0.03 mm) caliper PTFE (Teflon®) film.
3) Place the film "sandwich" between preheated aluminum plates that are inserted into a Carver Press model 3853-0 with heated plates set to approximately 200° C.
4) Heat the material for 3 minutes and then pressing it between the plates with an applied pressure of 17 MPa.
5) Allow the formulation to flow under pressure for 30 seconds.
6) Quench the resulting film to ambient temperature.
7) Cut the sample into three equal portions.
8) Place each portion between films of PTFE and preheated aluminum plates and allowed to heat up to 160° C. for 1 minute in the Carver press before 14 MPa of pressure is applied.
9) Allow the sample to flow under pressure for 30 seconds.
10) Release the pressure is removed and rotate the sample 90°. Insert the sample back into the press and immediately apply a pressure of 21 MPa.
11) The sample is again allowed to flow for 30 seconds. The pressure is released and the sample is flipped, inserted back into the press and immediately 28 MPa of pressure is applied.
12) The sampled is again allowed to flow for 30 seconds.
13) The pressure is removed and the sample is rotated 90° and inserted back into the press and immediately 34 MPa psi of pressure is applied.
14) The sample is again allowed to flow for 30 seconds.
15) After the final pressing, the sample is allowed to cool to ambient temperature. The resulting film thickness is between 4 mils up to 15 mils thick
16) Cut the resulting sample into a 2.5 cm×5 cm rectangle.

All testing is done at ambient laboratory conditions (~25° C., 50% RH).

First Strain (Shaping Strain) Hysteresis Cycle:

1) Samples are placed in the tensile tester jaws with a 2.5 cm gauge length. Otherwise, mount the sample between the jaws of the tensile tester using the maximum gap allowed by the sample length.
2) Strain the sample to a maximum strain of 200% (i.e., the sample is 3× its initial length) at a strain rate of 25.4 cm/min. Particular samples may be strained to other maximum strains in specific instances. If a maximum strain other than 200% is used, that strain should be recorded and used in the % Set calculation.
3) At 200% strain (7.5 cm jaw separation) the direction of jaw displacement is reversed and the jaw returns to its original position at a rate of 25.4 cm./min.
4) Allow the sample to relax at zero strain for one minute.
5) After one minute, the samples are reloaded at a strain rate of 25.4 cm./min up to a load of 0.10 N to pull out slack in the sample. Measure and record the separation between the jaws.
6) Calculate % set according to the following equation (The % set determines the extent of permanent plastic deformation built into the material as a result of the pre-straining process.):

$$\% \text{ Set} = \left[\frac{\text{Jaw Gap after Step 5} - \text{Gage Length}}{\text{Gage Length}}\right] \times 100$$

7) A minimum of 3 samples is tested and the data averaged.
8) Report the following:
   i) Maximum load at 200% strain (or other value of maximum strain) in N/cm.
   ii) % set (As will be recognized, the difference (100−% set) in turn provides the % extent of recoverable elastic deformation intrinsic to the material.)

Second Strain Hysteresis Cycle:

1) Clamp a sample prestrained according to the First Hysteresis Loading Cycle between a pair of jaws with set to a gage length of 2.5 cm pulling gently to remove any slack.
2) After 2 minutes, extend the sample to 50% strain (1.5× initial length) at a rate of 25 cm/min.

3) Hold the sample at 50% strain for a period of 30 seconds and the force is monitored (e.g., collected by the associated computer) as a function of time over that period.
4) Return to the original length at 10 in./min and hold for 60 seconds.
5) After one minute, the samples are reloaded at a strain rate of 25.4 cm./min up to a load of 0.10 N to pull out slack in the sample. Measure and record the separation between the jaws.
6) Measure the % set upon reloading following the same protocol described in the method outlined above.

$$\% \text{ Set} = \left[\frac{\text{Jaw Gap after Step 5} - \text{Gage Length}}{\text{Gage Length}}\right] \times 100$$

7) A minimum of 3 samples is tested and the data averaged.
8) Report the following for each of three samples:
   a. The load at 50% strain (N/cm)
   b. % set
   c. % force relaxation at 50% during the 30 second hold time in the second hysteresis cycle; It is determined using the following formula:

$$\% \text{ Force relaxation} = \frac{[(\text{Load at } 50\% \text{ before hold time}) - (\text{Load at } 50\% \text{ after hold time})]}{(\text{Load at } 50\% \text{ before hold time})}$$

Force Relaxation at Body Temperature (38° C.):
1) Clamp a sample prestrained according to the First Hysteresis Loading Cycle between a pair of jaws with set to a gage length of 2.5 cm pulling gently to remove any slack. For this test the jaws and sample are in an environmental chamber maintained at 38° C. and the sample is allowed to equilibrate in the chamber (~1 minute) before it is extended.
2) Extend the sample to 50% strain (1.5× initial length) at a rate of 25 cm/min.
3) Hold the sample at 50% strain for a period of 10 hours
4) Monitor and record the initial force after the extension step and the force at 1, 4 and 10 hrs at 38° C.
5) Calculate and report % force relaxation for three samples at each time period, using the following equation:

$$\% \text{ Force relaxation (at 38 C. \& at time } t) = \frac{[(\text{Initial load at } 50\%) - (\text{Load at time } t)]}{(\text{Initial load at } 50\%)}$$

Dimensional Stability in Storage Conditions
This method is based on ASTM standard method D 1204-02:
1) Prestrain a sample according to the First Hysteresis Loading Cycle
2) Carefully measure the length and width dimensions of the sample and a permanent marker is used to trace equidistant points at 10 or 5 mm intervals (depending upon the initial size of the specimens) in both dimensions.
3) Place the sample on a sand bed (replaces paper and talc of the ASTM method) and into a controlled thermal chamber at a temperature of 60° C.
4) Remove the sample after two minutes.
5) Measure both dimensions after the exposure to 60° C.
6) Calculate the change in both dimensions as a percentage of the original dimension. A value above 100% is indicative of an expansion of the material in that particular direction as a result of exposure to heat (annealing). A value lower than 100% is indicative of a contraction of the specimen.
7) Report the results for three samples.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An extruded web, said extruded web being selected from the group consisting of nonwovens and films and comprising a plasto-elastic material wherein said plasto-elastic material comprises a combination of an elastomeric polypropylene and a second polyolefin, said combination being selected from polymeric blends or polymeric mixtures, such that
   a) said material has substantially plastic properties when a sample taken from said web is subjected to an initial strain cycle such that said material is provided with a set of at least 30% by said initial strain cycle; and
   b) said material has substantially elastic properties when a sample taken from said web is subjected to at least a second strain cycle.

2. An extruded web according to claim 1 wherein said elastomeric polypropylene is a polypropylene polymer comprising crystalline isotactic blocks and amorphous atactic blocks.

3. An extruded web according to claim 1 wherein said second polyolefin is a polyolefin wax.

4. An extruded web according to claim 1 wherein said web is a nonwoven material.

5. An extruded web according to claim 4 wherein said nonwoven material is composed of fibers, said fibers being bicomponent fibers.

6. An extruded web according to claim 5 wherein said bicomponent fibers comprise an additional material having substantially elastomeric properties.

7. An extruded web according to claim 5 wherein said bicomponent fibers comprise an additional material having substantially plastic properties.

8. An extruded web according to claim 1 wherein said web comprises a film.

9. An extruded web according to claim 8 wherein said film is a coextruded film having at least one additional layer.

10. An extruded web according to claim 9 wherein said at least one additional layer comprises an additional material having substantially elastic properties.

11. An extruded web according to claim 9 wherein said at least one additional layer comprises an additional material having substantially plastic properties.

12. An extruded web, said extruded web being selected from the group consisting of nonwovens and films and comprising a plasto-elastic material wherein said plasto-elastic material comprises a combination of:
   a) an elastomeric polypropylene;
   b) a second polymeric material selected from the group consisting of a second polyolefin, styrenic block copolymers and combinations thereof; and
   c) a polyolefin wax;
   wherein said combination is selected from polymeric blends and polymeric mixtures;
   wherein said plasto-elastic material has substantially plastic properties when a sample taken from said web is subjected to an initial strain cycle and said material has substantially elastic properties when a sample taken from said web is subjected to a second strain cycle.

13. An extruded web according to claim 12 wherein said plasto-elastic material further comprises a second polyolefin wax.

14. An extruded web, said extruded web being selected from the group consisting of nonwovens and films and comprising a plasto-elastic material wherein said plasto-elastic material comprises a combination of:
   a) an elastomeric polypropylene; and
   b) a polyolefin wax;
   wherein said combination is selected from polymeric blends and polymeric mixtures;
   wherein said plasto-elastic material has substantially plastic properties when a sample taken from said web is subjected to an initial strain cycle and said material has substantially elastic properties when a sample taken from said web is subjected to a second strain cycle.

* * * * *